United States Patent [19]

Geering

[11] 4,299,841
[45] Nov. 10, 1981

[54] METHODS OF COMBATTING INSECTS AND ACARIDS

[75] Inventor: Quinton A. Geering, Cambridge, England

[73] Assignee: Fisons Limited, England

[21] Appl. No.: 83,544

[22] Filed: Oct. 10, 1979

Related U.S. Application Data

[63] Continuation-in-part of Ser. No. 711,376, Aug. 3, 1976, abandoned.

[30] Foreign Application Priority Data

Aug. 14, 1975 [GB] United Kingdom ............... 33835/75

[51] Int. Cl.$^3$ ..................... A01N 37/00; A01N 43/16; A01N 47/10; A01N 57/00
[52] U.S. Cl. .................................... 424/282; 424/216; 424/298; 424/300; 424/327; 424/DIG. 8
[58] Field of Search .......... 424/216, 282, 300, DIG. 8, 424/327, 298

[56] References Cited

U.S. PATENT DOCUMENTS 2,759,010 8/1956 Lorenz et al. ............... 424/DIG. 8
3,948,952 4/1976 Gates et al. ......................... 424/282

FOREIGN PATENT DOCUMENTS 1220056 11/1971 United Kingdom .

OTHER PUBLICATIONS

Kouskolekas et al., C.A., vol. 80 (1974) 104,819s.

Primary Examiner—Allen J. Robinson
Attorney, Agent, or Firm—Wenderoth, Lind & Ponack

[57] ABSTRACT

Insect and acarid pests, particularly those of crops, are combated by applying (a) 2,2-dimethyl-1,3-benzodioxol-4-yl N-methylcarbamate and (b) a soil applied systemic insecticide or acaricide, particularly immediately before planting the crop.

10 Claims, No Drawings

METHODS OF COMBATTING INSECTS AND ACARIDS

This is a continuation-in-part of Ser. No. 711,376, filed Aug. 3, 1976 now abandoned.

The present invention relates to a method of combatting insects and acarids, insecticidal and acaricidal compositions and their preparation.

The invention provides a method of combating insects or acarids at a locus infested or liable to be infested with them, which method comprises applying to the locus:

(A) 2,2-dimethyl-1,3-benzodioxol-4-yl N-methylcarbamate; and (B) a soil applied systemic insecticide or a soil applied systemic acaricide.

In addition, the invention provides an insecticidal or acaracidal composition comprising (A) and (B).

The present method and compositions are unexpectedly advantageous. Components (A) and (B) are synergistic, being surprisingly effective. The method and composition achieve a greater insecticidal or acaricidal effect, e.g. against insects or acarids which attack crops above ground, then the additive effect of the essential components. They are particularly useful against insect and acarid pests of crops.

The proportions of (A) to (B) can vary over a wide range depending on such factors as the particular locus to be treated, the particular pests to be combatted and the particular effect desired. Overall, however, the proportions of (A) to (B) may be for example from 1:20 to 5:1 respectively. There may be a greater weight of (B) than of (A), or a greater weight of (A) than of (B). Generally the proportions of (A) to (B) are from 5:1 to 1:2.5, preferably from 3:1 to 1:2, especially from 2:1 to 1:2, respectively. In a preferred embodiment, the proportions of (A) to (B) are 1:1-2.5 respectively. Parts, proportions and percentages in this specification are by weight unless otherwise indicated.

Component (B) is preferably one or more, preferably one, of aldicarb (2-methyl-2-(methylthio)propionaldehyde O-methylcarbamoyloxime), carbofuran (2,3-dihydro-2,2-dimethyl-7-benzofuranyl methylcarbamate), terbufos (S-tert-butylthiomethyl O,O-diethyl phosphorodithioate), phorate (O,O-diethyl S-ethylthiomethyl phosphorodithioate), disulfoton (O,O-diethyl S-2-ethylthioethyl phosphorodithioate), dimethoate (O,O-dimethyl S-methylcarbamoylmethyl phosphorodithioate), 3,3-dimethyl-1-methylthio-2-butanone O-methylcarbamoyloxime, acephate (O,S-dimethyl acetylphosphoramidothioate) or methomyl (1-[methylthio]ethylideneamino methylcarbamate).

Preferably (B) is 3,3-dimethyl-1-methylthio-2-butanone O-methylcarbamoyloxime.

The essential components (A) and (B) can be applied together in a composition comprising (A) and (B). The compositions can be prepared by admixing the ingredients. The compositions may initially be produced in the form of concentrates, e.g. containing 0.5-85% in toto of the essential components (A) and (B), and these may be diluted with water or a hydrocarbon, usually water, at the point of use for application by spraying, generally such that the concentration in toto of (A) and (B) is 0.02-3%, e.g. 0.1-3%, preferably 0.15-2%. In a preferred embodiment, however, the compositions are produced directly for application, e.g. in the form of dusts or granules. A preferred composition is in the form of granules containing 1.5-3% (A) and 3-5% (B), e.g. 1.5% (A) and 3.5% (B).

Thus, overall the present compositions may contain for example 0.02-85% in toto of (A) and (B).

The compositions normally contain a carrier and/or a surface active agent.

The carrier may be a liquid, e.g. water (e.g. water used to dilute a concentrate for application). An organic solvent may be present with the water though this is not usually employed.

The carrier may be a liquid other than water, for example an organic solvent, e.g. a water-immiscible solvent, for instance a hydrocarbon which boils within the range 130°-270° C., in which the essential components are dissolved or suspended. A concentrate containing an organic solvent may contain a surface active agent so that the concentrate acts as a self-emulsifiable concentrate on admixture with water.

The carrier may be a solid, which may be finely divided. Examples of suitable solids are limestone, clays, sand, mica, chalk, attapulgite, diatomite, perlite, sepiolite, silicas, silicates, lignosulphonates and solid fertilizers. The carrier can be of natural or synthetic origin or can be a modified natural material.

Wettable powders soluble or dispersible in water may be formed by admixing the essential components with or without a carrier with a surface active agent. Preferably, however, the essential components are admixed with a solid carrier to form a dust, powder or granular product.

The term 'surface active agent' is used in the broad sense to include materials variously called emulsifying agents, dispersing agents and wetting agents. Such agents are well known in the insecticide and acaricide art.

The surface active agents used may comprise anionic surface active agents, for example soaps, fatty sulphate esters such as dodecyl sodium sulphate, octadecyl sodium sulphate and cetyl sodium sulphate, fatty aromatic sulphonates such as alkyl-benzene sulphonates or butyl-naphthalene sulphonates, more complex fatty sulphonates such as the amide condensation product of oleic acid and N-methyl taurine or the sodium sulphonate of dioctyl succinate.

The surface active agents may also comprise non-ionic agents, for example condensation products of fatty acids, fatty alcohols or fatty substituted phenols with ethylene oxide, or fatty esters and ethers of sugars or polyhydric alcohols, or the products obtained from the latter by condensation with ethylene oxide, or the products known as block copolymers of ethylene oxide and propylene oxide.

The surface active agents may also comprise cationic agents, for example cetyl trimethylammonium bromide.

Preferred surface active agents include fatty alkyl sulphates, alkyl aryl sulphonates, fatty alkyl ethoxylates, sulphated fatty alkyl ethoxylates, dialkyl sulphosuccinate esters, the amide condensation product of oleic acid and N-methyl taurine, lignin sulphonate salts, sulphonated naphthalene-formaldehyde condensates and sulphonated urea-formaldehyde condensates.

The compositions can contain a coating of an adhesive agent, e.g. a cellulose ether, and this can prolong the residual activity by forming a coating, thus inhibiting the physical removal of the active ingredients e.g. by wind, rain or rubbing.

Instead of applying (A) and (B) together in a composition such as is discussed above, they can be applied separately in analogous compositions containing just (A) or (B), particularly as whole or part of a chemical insect or acarid control programme in a crop season. In a preferred sequence, (A) is applied at or immediately before planting a crop and (B) is applied after emergence of the crop. Both simultaneous and sequential application may be employed, e.g. a mixture of (A) and (B) applied at or immediately before planting a crop and (B) applied after emergence of the crop.

Preferably a mixture of (A) and (B) is applied.

(A) and (B) may be mixed immediately before use. Desirably, however, they would already have been mixed.

The invention provides a one pack presentation, in which (A) and (B) are already mixed, and also a single package designed to hold (A) and (B), e.g. in the form of compositions such as are discussed above, in separate containers, for mixing of (A) and (B), e.g. in a spray tank, for application.

A further pesticide can be used in sequence or admixture with component (A) or (B). For instance, (A) and (B) can be applied separately and a further pesticides applied with (A). Alternatively, a composition comprising a mixture of (A), (B) and the further pesticide can be applied. Usually the proportions of (A) to the further pesticide are from 1:10 to 20:1 e.g. from 1:10 to 10:1. The further pesticide can be a further insecticide or acaricide. It can also be a molluscicide, e.g. methiocarb (3,5-dimethyl-4-methylthiophenyl methylcarbamate) or metaldehyde, or a nematicide, e.g. fenamiphos (ethyl 3-methyl-4-(methylthio)phenyl 1-methylethylphosphoramidate), aldicarb (2-methyl-2-(methylthio)-propylideneamino methylcarbamate) or oxamyl (S-methyl-N',N'-dimethyl-N-(methylcarbamoyloxy)-1-thio-oximidate). The further pesticide is usually an acaricide, molluscicide or nematicide.

Fertilizers can be employed with the present essential pesticides.

Plants, the soil, land or aquatic or other areas can be treated by the present method. Preferably it is conducted outdoors or in greenhouses.

The present method and composition can be applied against a wide range of insect and acarid pests. They are of particular interest against insect pests. They are particularly useful against insect and acarid pests of crops (i.e. desired plants), which can be horticultural crops but are preferably agricultural crops, e.g. potatoes, maize, sugar beet, cotton, rice, wheat, citrus crops, sugar cane, brassica crops or tobacco, especially maize or sugar beet. Thus, the method and composition are preferably applied to a locus at which a crop is growing or is to grow. Preferably, the mixture of essential pesticides, or one of them where the other is applied later, is applied at or immediately before planting; it may be incorporated in the soil immediately before planting. Preferably both (A) and (B) are soil applied, when (A) dramatically enhances the effect of (B).

The method and composition are useful against soil borne insect or acarid pests of desired plants, such as wireworms of the genus Agriotes, pygmy beetle *Atomaria linearis*, millipedes, Symphylans, Collembola and cutworms e.g. Agrotis spp. They are also useful against insect or acarid pests which attach desired plants above ground, such as mangold fly (*Pegomyia betae*), aphids e.g. *Myzus persicae* and *Aphis fabae*, leaf hoppers, e.g. rice leaf hoppers, scale insects and mealy bugs.

The term 'insect' is used herein in the sense given in Webster's New International Dictionary, 2nd edition (1958) as meaning 'any of numerous small invertebrate animals generally having the body more or less obviously segmented. They belong to the class Insecta, comprising six-legged, usually winged forms, as beetles, bugs, bees, files, etc, and to other allied classes of arthropods whose members are wingless and usually have more than six legs, as spiders, mites, ticks, centipedes, wood lice, etc'. Thus, the term is used herein to include millipedes and Symphyla.

The present method is especially employed at such rates that ¼–2, preferably ¾–1, kg in toto of (A) and (B) is applied per hectare. Preferably 150–360 g, for example 200–360 g, e.g. 240 g, of (A) are applied per hectare, and preferably 200–800 g, for example 400–700 g, e.g. 560 g, of (B) are applied per hectare.

The invention is illustrated by the following Examples:

EXAMPLE 1

The separate and combined effects of (A) 2,2-dimethyl-1,3-benzodioxol-4-yl N-methylcarbamate and (B) 3,3-dimethyl-1-methylthio-2-butanone O-methylcarbamoyloxime were assessed in a trial on sugar beet in France in 1976. (A) was employed as 3% granules and (B) as 5% granules. Pelleted sugar beet seed, containing 480 g per 100 kg of seed of the standard fungicide thiram (tetramethylthiuram disulphide), was planted in furrows and (A), (B) or (A) plus (B) were distributed along the furrows at the rates of active ingredient given in the Table below. On control plots no (A) or (B) was employed. Each treatment was carried out on a plot of 20 plants, and each treatment was replicated 4 times.

The soil was moist at the time of drilling. An exceptionally dry growing season ensued.

There was no evidence of soil pests in the trial.

11 Weeks after drilling, the number of aphids (*Aphis fabae*) on the plants in each plot was assessed. Mean results are as follows:

| Treatment | Rate, g per hectare | No of Aphids on 20 plants |
| --- | --- | --- |
| (A) | 453 | 166.5 |
| (B) | 555 | 61.8 |
| (A) + | 320 | |
| (B) | 555 | 16.0 |
| Control | | 204.8 |

This Example shows the dramatic improvement produced by the combination according to the invention.

EXAMPLE 2

Combinations of (A) bendiocarb (2,2-dimethyl-1,3-benzodioxol-4-yl N-methylcarbamate) and (B) thiofanox (3,3-dimethyl-1-methylthio-2-butanone O-methylcarbamoyloxime) were employed at the rates listed in the Table below on sugar beet in the field. The number of green aphids per 10 plants was assessed after the treatments had had time to work. The mean results for 4 replicates were as follows:

| | Rates, g per ha | | |
| --- | --- | --- | --- |
| Experiment | Bendiocarb | Thiofanox | Aphids per 10 Plants |
| Control | 0 | 0 | 15.3 |
| 1 | 300 | 200 | 11.5 |
| 2 | 225 | 450 | 2.25 |
| 3 | 300 | 600 | 5.75 |
| 4 | 150 | 400 | 4.5 |
| 5 | 225 | 600 | 3.5 |

-continued

| | Rates, g per ha | | |
|---|---|---|---|
| Experiment | Bendiocarb | Thiofanox | Aphids per 10 Plants |
| 6 | 300 | 800 | 6.5 |

This Example shows the utility of various proportions and rates of active ingredients.

EXAMPLE 3

(A) bendiocarb (2,2-dimethyl-1,3-benzodioxol-4-yl N-methylcarbamate) and (B) phorate (O,O-diethyl S-ethylthiomethyl phosphorodithioate) were employed separately and together at the rates listed in the Table below on sugar beet in the field. The number of black aphids per 10 plants was assessed after the treatments had had time to work. The mean results for 4 replicates were as follows:

| | Rates, g per ha | | |
|---|---|---|---|
| Experiment | Bendiocarb | Phorate | Aphids per 10 Plants |
| 1 | 300 | 0 | 12.8 |
| 2 | 0 | 500 | 12.5 |
| 3 | 150 | 250 | 7.8 |

This Example shows the utility of a different (B) pesticide, and demonstrates the dramatic improvement produced by the combination according to the invention.

EXAMPLE 4

(A) bendiocarb (2,2-dimethyl-1,3-benzodioxol-4-yl N-methylcarbamate) and (B) thiofanox (3,3-dimethyl-1-methylthio-2-butanone O-methylcarbamoyloxime) were employed separately and together at the rates listed in the Table below on sugar beet in the field. The control of wireworm was assessed by counting the number of plants surviving in 32 meters of plant row; the more wireworm that remain the fewer the number of surviving plants. The mean results for 4 replicates were as follows:

| | Rates, g per ha | | |
|---|---|---|---|
| Experiment | Bendiocarb | Thiofanox | Plants per 32 meters |
| Control | 0 | 0 | 19.5 |
| 1 | 0 | 800 | 19.3 |
| 2 | 276 | 0 | 27.25 |
| 3 | 300 | 200 | 35.0 |

It can be seen that thiofanox alone even at 800 g per hectare is ineffective, but that employing one quarter of this amount of ineffective material with the bendiocarb dramatically improves the effect of the bendiocarb.

EXAMPLE 5

The pesticides shown in the Table below were applied to sugar beet in the field at the rates shown. The control of wireworm was assessed by counting the number of plants surviving in 32 meters of plant row, compared to untreated controls. The more wireworms that remain the fewer the number of surviving plants. The mean results for 4 replicates were as follows:

| | Rates, g per ha | | | Plants |
|---|---|---|---|---|
| Experiment | Bendiocarb | Phorate | Thiofanox | per 32 meters |
| 1 | 150 | 250 | 0 | 143.0 |
| 2 | 225 | 425 | 0 | 138.8 |
| 3 | 300 | 800 | 0 | 129.0 |
| 4 | 300 | 0 | 800 | 129.5 |
| Control | 0 | 0 | 0 | 107.0 |

EXAMPLE 6

Phorate at 500 g per hectare and bendiocarb plus phorate at the rate shown in the table below were applied to sugar beet in the field. The number of black aphids per 10 plants was assessed after the treatments had had time to work. The mean results for 4 replicates were as follows:

| | Rates, g per ha | | |
|---|---|---|---|
| Experiment | Bendiocarb | Phorate | Aphids per 10 Plants |
| 1 | 0 | 500 | 12.5 |
| 2 | 225 | 425 | 10.3 |

I claim:
1. A method of combatting insects or acarids at a locus infested or liable to be infested with them, which method comprises applying to the locus an insect or acarid combatting amount of:
   (A) 2,2-dimethyl-1,3-benzodioxol-4-yl N-methylcarbamate; and
   (B) 3,3-dimethyl-1-methylthio-2-butanone O-methylcarbamoyloxime,
   the weight proportions of (A) to (B) being from 2:1 to 3:8 respectively.
2. The method according to claim 1 wherein a mixture of (A) and (B) is applied simultaneously.
3. The method according to claim 1 wherein a crop is growing at the locus.
4. The method according to claim 1 wherein a crop is to grow at the locus.
5. The method according to claim 4 wherein the crop is maize or sugar beet.
6. The method according to claim 1 wherein the weight proportions of (A) and (B) are from 2:1 to 1:2 respectively.
7. The method according to claim 1 wherein the weight proportions of (A) to (B) are 1:1–2.5 respectively.
8. An insecticidal or acaracidal composition comprising:
   (A) 2,2-dimethyl-1,3-benzodioxol-4-yl N-methylcarbamate; and
   (B) 3,3-dimethyl-1-methylthio-2-butanone O-methylcarbamoyloxime,
   the weight proportions of (A) to (B) being from 2:1 to 3:8 respectively.
9. The composition according to claim 8 wherein the weight proportions of (A) to (B) are from 2:1 to 1:2 respectively.
10. The composition according to claim 8 wherein the weight proportions of (A) to (B) are 1:1–2.5 respectively.

* * * * *